United States Patent [19]

Utsugi

[11] Patent Number: 4,466,443
[45] Date of Patent: Aug. 21, 1984

[54] ULTRASONIC DIAGNOSTIC APPARATUS FOR EXAMINATION OF A COELIAC CAVITY

[75] Inventor: Mikio Utsugi, Tokyo, Japan

[73] Assignee: Olympus Optical Co., Ltd., Tokyo, Japan

[21] Appl. No.: 363,409

[22] Filed: Mar. 30, 1982

[30] Foreign Application Priority Data

Apr. 8, 1981 [JP] Japan .................................. 56-52837

[51] Int. Cl.³ .............................................. A61B 10/00
[52] U.S. Cl. ........................................ 128/660; 128/4
[58] Field of Search ................. 128/660, 4, 6, 661, 128/663

[56] References Cited

U.S. PATENT DOCUMENTS 4,375,818 3/1983 Suwaki et al. ..................... 128/660

OTHER PUBLICATIONS

Hisanaga, K. et al., "A Trans-Esophageal Real-Time Sector Scanner with an Oil-Filled Cell", Prod. of 23rd Ann. AIUM, 1978.

Primary Examiner—Kyle L. Howell
Assistant Examiner—Francis J. Jaworski
Attorney, Agent, or Firm—Frishauf, Holtz, Goodman & Woodward

[57] ABSTRACT

An ultrasonic diagnostic apparatus for examination of a coeliac cavity, wherein a chamber sealed from the outside is provided near the distal end portion of an insertion section. An ultrasonic scanning motor provided with an ultrasonic transducer is held in the sealed chamber. This ultrasonic scanning rotor is rotated by a force supplied from a drive power source in an operation section through the rotation torque-transmitting member. A drive passage through which the rotation torque-transmitting member extends communicates with the sealed chamber. That portion of the drive passage which is located near the operation section is sealed by a packing. The drive passage and sealed chamber are filled with a liquid ultrasonic-permeable medium.

16 Claims, 4 Drawing Figures

ULTRASONIC DIAGNOSTIC APPARATUS FOR EXAMINATION OF A COELIAC CAVITY

BACKGROUND OF THE INVENTION

This invention relates to an ultrasonic diagnostic apparatus, and more particularly to an ultrasonic diagnostic apparatus for examination of a coeliac cavity.

The scanning process of an ultrasonic diagnostic apparatus for examination of a coeliac cavity is generally carried out electronically or mechanically. With an electronic scanning type ultrasonic diagnostic apparatus, a large electronic scanning type ultrasonic transducer is set near the distal end of the insertion section of said diagnostic apparatus, thereby undesirably widening its thickness in the proximity of the distal end of the insertion section. With a mechanical scanning type ultrasonic diagnostic apparatus, a relatively large rotation power source section can be set in the operation section, making it unnecessary to use a thick insertion section. However, the mechanical scanning type ultrasonic diagnostic apparatus has the following drawbacks. It is necessary to use a rotation torque-transmitting wire for the rotation of an ultrasonic transducer or ultrasonic reflection mirror provided in the proximity of the distal end of the insertion section. This rotation torque-transmitting wire is conducted through the elongate insertion section to transmit the rotation torque of the rotation power source to the transducer or mirror. A scanning mechanism containing the transducer or mirror is received in a chamber filled with a liquid ultrasonic transmission medium. The opening of the distal end of the rotation torque-transmitting wire passage is sealed in a liquid-tight state in order to prevent said liquid ultrasonic transmission medium from leaking to the operation section through said rotation torque-transmitting wire passage. Therefore, the rotation torque-transmitting wire undergoes resistance resulting from friction with the sealed section. The rotation member, such as a mirror is rotated in the liquid ultrasonic transmission medium, thereby imposing a considerable twisting force on the rotation torque-transmitting wire. Therefore, said wire fails to properly transmit the rotation torque. The flexible wire passing through the flexible insertion section readily tends to be twisted. Therefore, when the rotation torque must be properly transmitted, then it is necessary to use a thick rotation torque-transmitting wire. This unavoidably causes the insertion section to be formed relatively thick, thereby undesirably imparting great pain to an examinee.

SUMMARY OF THE INVENTION

It is accordingly an object of the present invention to provide an ultrasonic diagnostic apparatus for examination of a coeliac cavity, wherein a rotation torque-transmitting member can properly conduct a driving force to a scanning member; and a narrow rotation torque-transmitting member can be applied, thereby reducing the thickness of the insertion section.

To attain the above-mentioned object, the invention provides an ultrasonic diagnostic apparatus for examination of a coeliac cavity, which comprises:

an elongated insertion section; and
an operation section connected to the proximal end of said insertion section, and wherein said insertion section is formed of:

a chamber provided near the distal end of said insertion section;

an ultrasonic transducer held in said chamber and provided with a rotatable ultrasonic scanning member;

a passage running through the insertion section, one end of which communicates with the chamber, and the other end of which extends to the operation section;

a rotation torque-transmitting member which loosely extends through the passage, and whose distal end is connected to the ultrasonic scanning member;

means for sealing that opening of the passage through which the rotation torque-transmitting member passes, which opening faces the operation section; and a liquid ultrasonic transmission medium filled in the passage and chamber; and said operation section is comprised of a scanning drive power source connected to the proximal end of the rotation torque-transmitting member.

DETAILED DESCRIPTION OF THE PREFERRED EMBODIMENTS

Figure 1:
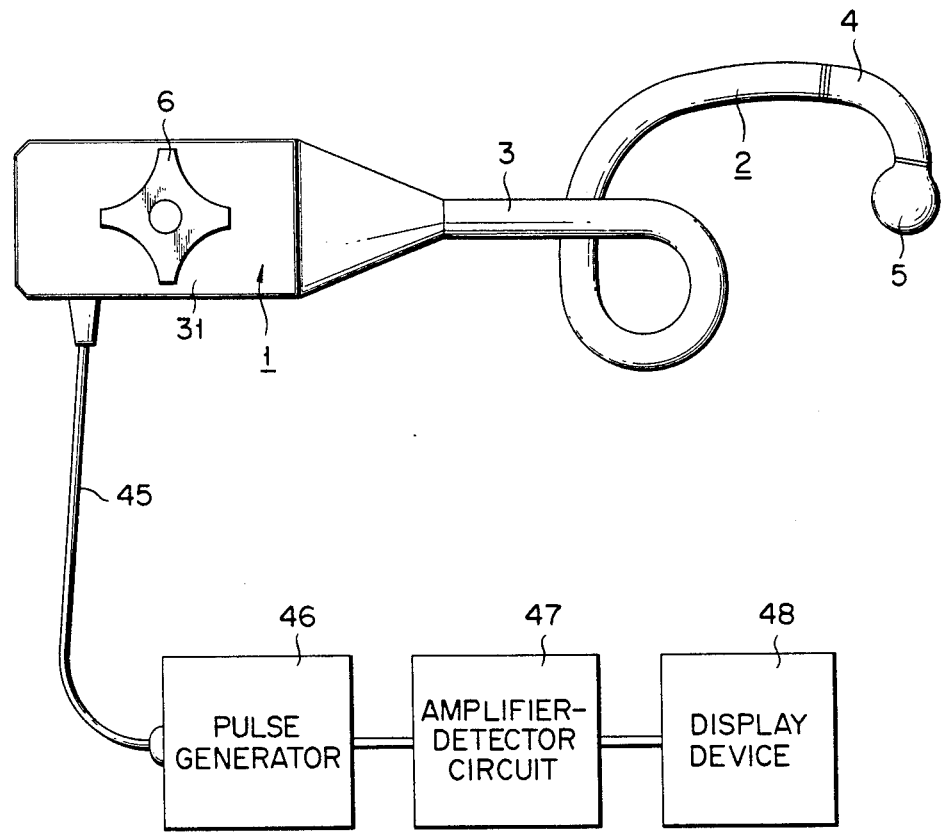
FIG. 1 is a schematic side view of the whole of an ultrasonic diagnostic apparatus according to a first embodiment of the invention for examination of a coeliac cavity.

FIG. 1 shows an operation section 1 of an ultrasonic diagnostic apparatus according to a first embodiment of the invention, for examination of a coeliac cavity. The proximal end of an elongated flexible insertion section 2 is connected to the operation section 1. The distal end of a flexible tube 3 of the insertion section 2 is connected to a distal end section 5 through a bendable tube 4. When an operation wire (not shown) extending through the insertion section 2 is pulled down by actuating a knob 6 of the operation section 1, the bendable tube 4 is bent to change the direction in which said distal end section 5 is set in place. As seen from FIG. 2, a chamber 8 open on one side is provided in the body 7 of the distal end section 5. Held in said chamber 8 is a scanning member 9 for scanning with ultrasonic beams. The scanning member 9 is constructed as follows. A rotor 10 acting as an ultrasonic scanning member is set in the chamber 8 in a state rotatable around a line parallel with the axis of the insertion section 2. The shaft 11 of the rotor 10 is loosely fitted into a hole 12 extending through the walls of the body 7 and is rotatably supported. Mounted on part of the outer peripheral wall of the rotor 10 is an ultrasonic transducer 13 consisting of an ultrasonic oscillation element (for example, a piezoelectric element) for issuing or receiving ultrasonic waves, with an ultrasonic damper 14 interposed therebetween. The ultrasonic transducer 13 is set in a direction perpendicular to the axis of the insertion section 2 around which the rotor 10 is rotated. A pair of stranded signal cables 15, 15 are connected to the ultrasonic transducer 13. The stranded signal cables 15, 15 extend through a hole 16 formed in the rotor 10 and its shaft 11 and then through a later described rotation torque-transmitting member 17, up to the operation section 1. The rotation torque-transmitting member 17 is constructed by helically winding, for example, a metal wire 18 with adjacent turns closely attached to each other. The wire 18 is wound in such direction as to cause the windings to tighten further when rotation torque is transmitted through the member 17.

The distal end of the rotation torque-transmitting member 17 is connected to the shaft 11 of the rotor 10. Closely attached airtight to the outer periphery of the shaft 11 and rotation torque-transmitting member 17 is a tube 19 prepared from a material having a small friction coefficient, for example, tetrafluoroethylene or a copolymer consisting of tetrafluoroethylene and hexafluoropropylene.

A tubular flexible guide 21 prepared from synthetic resin extends through the insertion section 2. The interior region of said guide 21 constitutes the passage 20 for the rotation torque-transmitting member 17. The distal end of said guide 21 is connected airtight to the body 7 of the distal end section 5. The passage 20 communicates with the chamber 8 through the shaft hole 12. The guide 21 contain a tube 22 prepared from a material having a small friction coefficient, for example, tetrafluoroethylene or a copolymer consisting of tetrofluoroethylene and hexafluoropropylene. The outer peripheral wall of the tube 22 is covered with a metal wire braid 23.

The rear end face of the rotor 10 is fitted with an optical reflection mirror 24. The end portion of an optical signal transmission fiber 25 and that of an optical signal reception fiber 26 are set in parallel on the inner wall of the chamber 8 which wall faces the optical reflection mirror 24. The optical fibers 25, 26 extend through the insertion section 2 to the operation section 1 and are respectively connected to an optical signal detector (not shown). The optical reflection mirror 24, optical signal transmission fiber 25, optical signal reception fiber 26, and optical signal detector jointly constitute means for detecting the angle through which the rotor 10 has been rotated. When the rotor 10 is rotated to cause the optical reflection mirror 24 to face the end portions of both optical fibers 25, 26, then a beam of light emitted from the optical signal transmission fiber 25 is reflected by the mirror 24 to enter the optical signal reception fiber 26. A light beam entering the optical signal reception fiber 26 is converted into an electrical signal by an optical signal detector (not shown). Thus, the rotated position of the rotor 10 used for ultrasonic scanning or transmission and reception of an optical signal, can be detected. A signal denoting the detected rotated position of the rotor 10 is supplied to a later described display device, thereby controlling a display operation. A bag-shaped balloon 27 prepared from elastic rubber material encloses the distal end section 5 including the opening of the chamber 8. The edge 28 at the opening of the ballon 27 is tightly fixed to the outer peripheral wall of the body 7 of the distal end section 5. A projecting central portion 27a of the bag-shaped balloon 27 is fixed to the outer end of the body 7 of the distal end section 5.

The body 7 of the distal end section 5 is fitted with a port 29 which communicates with the interior of the balloon 27 to discharge air and liquid ultrasonic permeable medium 37 port 29 is hereinafter simply referred to as "a discharge port"). The discharge port 29 is open to the outer peripheral wall of one side of the body 7 of the distal end section 5. The discharge port 29 communicates with a flexible pipe 30 extending through the insertion section 2 which is used to discharge air and liquid ultrasonic transmission medium (pipe 30 is hereinafter simply referred to as "a discharge pipe"). The discharge pipe 30 extends to the operation section 1.

Figure 3:
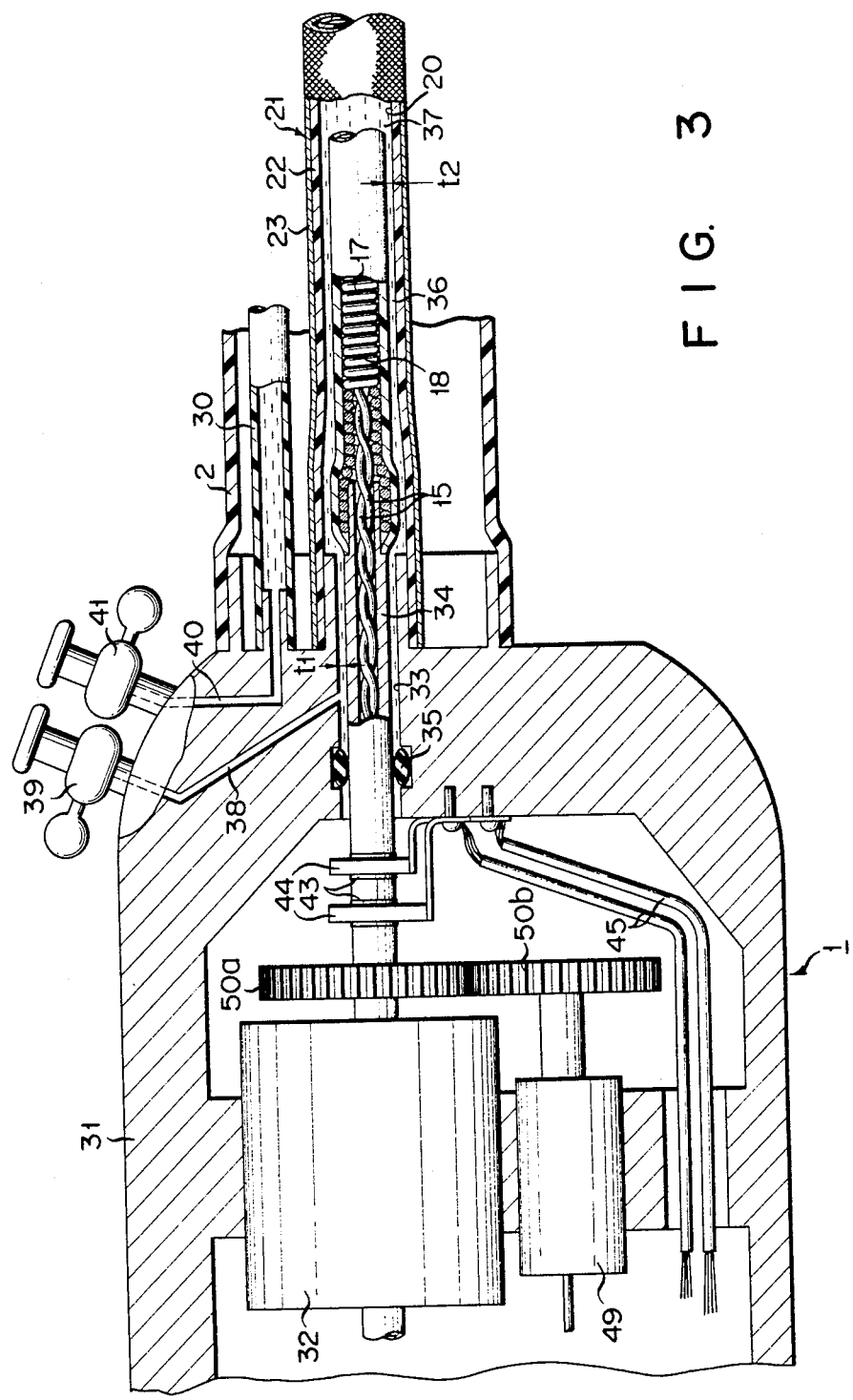
FIG. 3 is a longitudinal sectional view of a junction between the operation section, and insertion section and the proximity of said junction.
Figure 4:
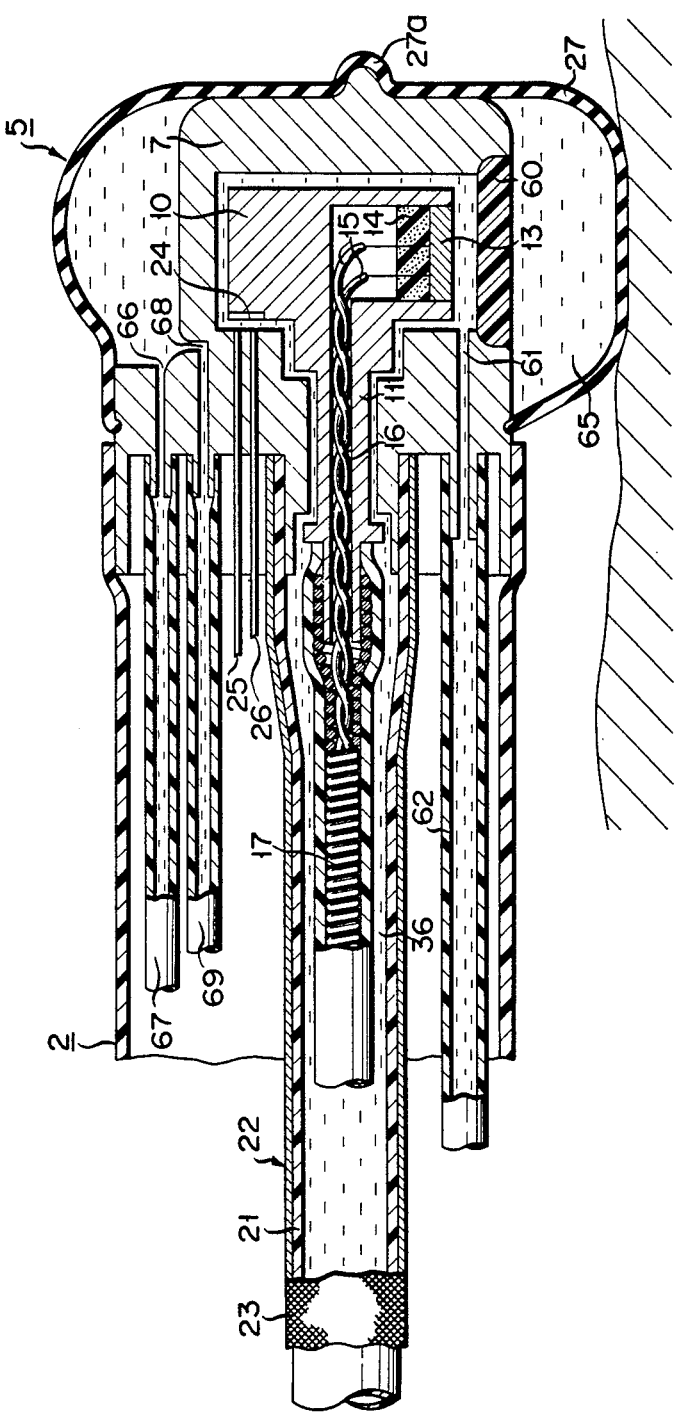
FIG. 4 is a longitudinal sectional view of the distal end portion of an ultrasonic diagnostic apparatus according to a second embodiment of the invention.

The operation section 1 is arranged as shown in FIG. 3. A device 32 acting as a drive source for ultrasonic scanning is provided in the body 31 of the operation section 1. The drive device 32 is formed of, for example, an electric motor. This drive device 32 rotates a hollow rotary shaft 34, which is rotatably supported in a shaft passage 33 which extends through the body 31 of the operation section 1 and also through the insertion section 2. A space between the outer peripheral wall of the hollow rotary shaft 34 and the inner peripheral wall of the shaft passage 33 is tightly closed by a sealing member 35 made of an elastic ring packing. This sealing member 35 seals the proximal end portion of the shaft passage 33 which faces the operation section 1. The shaft passage 33 constitutes part of the aforementioned passage for the rotation torque-transmitting member 17. That side of the hollow rotary shaft 34 which faces the drive device 32 is closed. The inner end of the rotary shaft 34 is connected to the proximal end of the rotation torque-transmitting member 17. Said rotary shaft 34 substantially constitutes part of the rotation torque-transmitting member 17 which transmits the rotation torque of the drive device 32 to the ultrasonic scanning rotor 10 used for transmission and reception of an ultrasonic signal. The proximal end of the guide 21 allowing for the passage of the rotation torque-transmitting member 17 is connected airtight to the body 31 of the operation section 1. The interior of the guide 21 communicates with the shaft passage 33. A space 36 is formed between the shaft passage 33 and rotary shaft, between the guide 21 and rotation torque-transmitting member 17, and between that portion of the shaft hole 12 which faces the distal end section 5 and the rotor shaft 11. The above-mentioned space 36 is filled with an ultrasonic permeable medium 37 such as deaerated water (corresponding to deep sea water or water filled in a pressurized water tank or pressurized dome) or silicone oil. The space 36 communicates with the chamber 8 of the distal end section 5, thereby enabling the ultrasonic permeable medium 37 to be supplied to the interior of the balloon 27 including the chamber 8 through said space 36.

Irrespective of the material of the ultrasonic permeable medium 37, the space 36 is chosen to have at least the following measurements. Namely, the width tl of said space 36 at the shaft passage 12 (FIG. 2) or shaft passage 33 (FIG. 3), i.e., half the difference between the outer diameter of the shaft 11 and the inner diameter of the shaft passage 12 or between the outer diameter of the rotary shaft 34 and the inner diameter of the shaft passage 33, is chosen to be 0.02 mm or over. Further at the guide 21, the width t2 of said space 36, that is, half the difference between the inner diameter of the passage 20 of the rotation torque-transmitting member 17 and the outer diameter of said member 17, is chosen to be 0.05 mm or over. In other words, said space 36 is arranged to fall within such a level as prevent the rotation torque-transmitting member 17 extending through the guide 21, from being undesirably shaken. Therefore, the liquid ultrasonic permeable medium 37 can flow easily, and the rotation torque-transmitting member 17 and ultrasonic scanning rotor 10 can be smoothly rotated.

Provided in that portion of the shaft passage 33 of the operation section 1 which lies nearer to the distal end than the sealing member 35, is an air or liquid inlet passage 38 in communication with said shaft passage 33. The outer end of said inlet passage 38 is fitted with a cock 39 acting as a port allowing for the influx of the ultrasonic-permeable medium 37. Said inlet port communicates with the chamber 8 through the passage 20 for the rotation torque-transmitting member 17. The operation section 1 is provided with an air or liquid discharge pipe 40 connected to the discharge pipe 30. The other end of said discharge pipe 40 is fitted with a cock 41 acting as a port allowing for the discharge of a liquid ultrasonic permeable medium 37.

The outer periphery of that portion of the rotary shaft 34 which projects into the operation section 1, is fitted with a pair of circular electric contacts 43, 43 which are respectively electrically connected to the aforementioned paired signal cables 15, 15. The contacts 43, 43 are each slidably contacted by a brush 44. An electric signal is drawn out from the cables 15, 15 through the contacts 43, 43 and brushes 44, 44 or supplied to said cables 15, 15 therethrough. The brushes 44 are connected to externally provided pulse generator 46 and amplifier-detector circuit 47. The amplifier-detector circuit 47 is connected to a display device 48 provided with a Braun tube. The above-mentioned pulse generator 46, amplifier-detector circuit 47 and display device 48 are detailed in a U.S. Pat. application (Ser. No. 258,004) entitled "Ultrasonic Diagnostic Apparatus for Endoscope" filed on Apr. 27, 1981.

The degree of rotation angle supplied to the rotation torque-transmitting member 17 is indicated by a rotation angle detector 49 set in the operation section 1. Said rotation angle detector 49 detects the amount of rotation delivered from the rotary shaft 34 through gears 50a, 50b. The rotation angle detector 49 comprises, for example, an encoder which optically reads a pattern appearing on a disc scale fitted to a rotary shaft rotating with the gear 50b. Said rotation angle detector 49 may also be formed of a potentiometer.

Description is now given of the manner in which an ultrasonic diagnostic device embodying the invention is used for examination of a coeliac cavity, and the function of said device.

Figure 2:
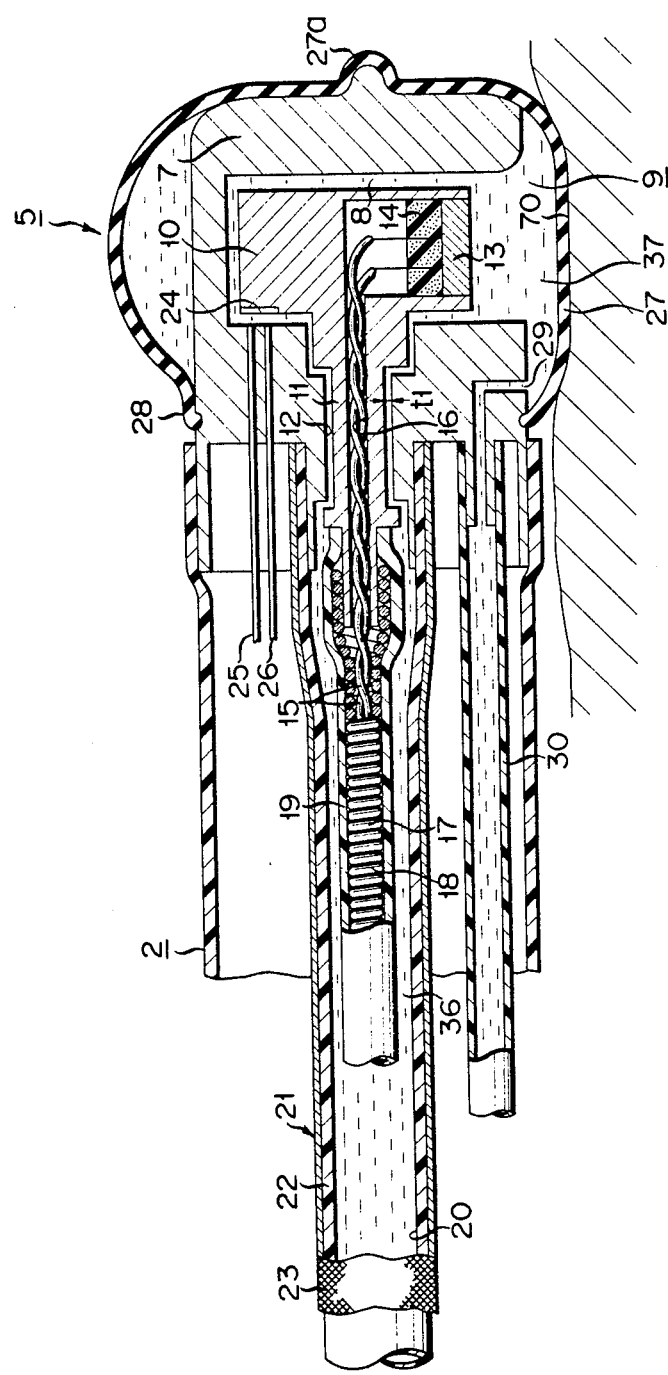
FIG. 2 is an enlarged longitudinal sectional view of the distal end portion of said diagnostic apparatus.

In operation, the insertion section 2 is put into a coeliac cavity, for example, the stomach. If the ultrasonic diagnostic device is so arranged as to function as the known endoscope, then the device can be put into the coeliac cavity while observation is made of said cavity. The distal end section 5 is drawn closest to an object of diagnosis. While the opening of the chamber 8 is set near the wall of the object of diagnosis, a liquid ultrasonic permeable medium-pouring device (not shown) is connected to the liquid inlet cock 39. A liquid ultrasonic permeable medium 37 is poured into the diagnostic device with the inlet cock 39 and discharging cock 41 left open. As a result, the liquid ultrasonic permeable medium 37 forces out air left in the space 36 provided in the passage 20 of the rotation torque-transmitting member 17, and is filled in said space 36, and then flows into the chamber 8 (FIG. 2). When the chamber 8 and balloon 27 are filled with the liquid ultrasonic permeable medium 37, then said balloon 27 is expanded. At this time, air remaining in the chamber 8 and balloon 27 are drawn out through the discharge pipes 29, 30 and 40 and discharge cock 41 in turn. As a result, the chamber 8 and balloon 27 are fully filled with the liquid ultrasonic permeable medium 37. When the balloon 27 swells, its wall is tightly pressed against a wall 70 of the object of diagnosis in the coeliac cavity (FIG. 2).

At this time, the pulse generator 46 and drive device 32 are actuated. The rotation torque of said drive device 32 turns the ultrasonic scanning rotor 10 by means of the rotation torque-transmitting member 17. The passage 20 for said rotation torque-transmitting member 17 which is filled with the liquid ultrasonic permeabile medium 37, is prevented from being mechanically compressed with a great force. The rotation torque-transmitting member 17 is lubricated by the liquid ultrasonic permeable medium 37. Therefore, the rotation torque of the drive device 32 is exactly transmitted to the ultrasonic scanning rotor 10 without being lost on the way.

An ultrasonic beam emitted from the transducer 13 propagates through the liquid ultrasonic permeable medium 37, balloon 27 and then the tissue of an examinee. The ultrasonic beam is reflected in accordance with the intra-tissue condition of the human body. The reflected ultrasonic beam is returned to the ultrasonic transducer 13 for detection. An electric detection signal delivered from the ultrasonic transducer 13 is transmitted through the signal cables 15, 15, contacts 43, 43, brushes 44, 44 and signal cables 45, 45. The detection signal is supplied to the pulse generator 46 and amplifier-detector circuit 47, causing a tomographic image of the internal organs to be indicated on the display device 48. Ultrasonic beams issued from or received by the ultrasonic transducer 13 are radially moved over a plane intersecting the axis of the insertion section 2 at right angles. This plane is used for display. Where an ultrasonic tomographic image is to be indicated on the display device 48, it is necessary to obtain information on the intensity of a reflected ultrasonic beam (magnitude of amplitude) and information on that spot of the display device 48 at which the tomographic image is to be indicated. Spot information for the tomographic image is determined by measuring the amount of rotation of the ultrasonic scanning rotor 10. The rotational measurement is made by the rotational angle dectector 49. The detector 49 begins measuring when the electric signal corresponding to the light beam reflected by the mirror 24 and transmitted through the optical signal reception fiber 26 is detected.

Description is now given of an ultrasonic diagnostic apparatus according to a second embodiment of the invention. With this second embodiment, the opening of the chamber 8 is fitted with a hard partition board 60 prepared from, for example, a plastics material highly permeable to ultrasonic beams and giving rise to little attenuation of reflected ultrasonic beams. The partition board 60 isolates the chamber 8 from the interior of the balloon 27. The second embodiment further comprises discharge pipes 61, 62 communicating with the chamber 8, inlet pipes 66, 67 allowing for the supply of a liquid ultrasonic permeable medium 65 to the interior of the balloon 27, and discharge pipes 68, 69 allowing for the withdrawal of said liquid ultrasonic permeable medium 65 from the balloon 27. The material of the liquid ultrasonic permeable medium 65 supplied to the chamber 8 is selected with importance mainly attached to the lubricating property of said medium. For the object of this invention, therefore a material having a high lubricating property such as silicone oil is applied, though it has a somewhat low property of propagating ultrasonic waves. A liquid ultrasonic permeable medium supplied to the interior of the balloon 27 is formed of, for example, deaerated water which is least likely to impart danger to a living body in case the balloon 27 happens to break. Even though a liquid ultrasonic permeable medium supplied to the chamber 8 may be formed of such material as has a relatively low propagating property, no important problem is raised, because the distance between the ultrasonic transducer 13 and partition board 60 is short.

This invention is not limited to the foregoing embodiments, but is applicable in various modifications. Namely, the rotatable shaft support may be provided with, for example, ball bearings. The rotation torque-transmitting member 17 may be formed of double tightly attached helical coils with an insulating material interposed therebetween. In this case, the coiled strands themselves may be utilized as signal cables. The supply and discharge of the respective liquid ultrasonic permeable mediums may be effected in the opposite direction to that which is used in the aforementioned embodiments. Further, it is not necessary to provide a separate guide in the insertion section 2. When the insertion section 2 is initially made from a solid bar, it is possible to drill a penetrating passage in said solid bar and use said penetrating passage as a guide. Throughout the previously described embodiments, a rotor is directly connected to a rotation torque-transmitting metal wire. However, this arrangement need not be restrictively followed. Namely, it is possible to let the distal end portion of the rotation torque-transmitting member include a gear transmission mechanism and connect said rotation torque-transmitting member to the rotor through said gear transmission mechanism. The rotation center of the ultrasonic scanning rotor need not be aligned with the axis of the insertion section. It is possible to let said rotation center accord with the axis of the insertion section by means of a spur gear or incline said rotation center to said axis by means of a bevel gear.

As described above, the present invention enables an insertion section to be rendered very narrow and flexible. The rotation torque-transmitting member is immersed in a liquid ultrasonic permeable medium, prevented from being mechanically compressed, and moreover lubricated by said medium. Consequently, rotational torque is not lost during transmission, nor is the rotation torque-transmitting member twisted. Namely, the possibility of applying a flexible, narrow rotation torque-transmitting member can render the insertion section narrow and flexible. The sealing of the passage of the rotation torque-transmitting member is effected in the operation section. The resultant frictional force is substantially insufficient to cause the intermediate portion of the rotation torque-transmitting member to be undesirably twisted, thus assuring reliable sealing of said passage.

What is claimed is:

1. An ultrasonic diagnostic apparatus for examination of a coeliac cavity, comprising:

an insertion section including a distal end portion to be inserted into a coeliac cavity, the distal end portion forming a chamber sealed from the outside, a proximal end portion to be set outside of the coeliac cavity, said insertion section having a longitudinal axis and a drive passage extending from the chamber at the distal end portion to the proximal end portion along said longitudinal axis;

an operation section connected to the proximal end portion of the insertion section;

ultrasonic transducer means including an ultrasonic scanning member rotatably arranged in said chamber;

a rotation torque-transmitting member which loosely extends through said drive passage, one end of the rotation torque-transmitting member being operatively connected to the ultrasonic scanning member, and the other end extending to the operation section;

a liquid ultrasonic permeable medium contained in said chamber for filling said chamber and said drive passage;

sealing means at the operation section for sealing the proximal end portion of said drive passage to prevent said liquid ultrasonic permeable medium in said drive passage from entering a portion of the operation section; and a drive power source arranged at the operation section and connected to said other end of the rotation torque-transmitting member to rotate the ultrasonic scanning member through said rotation torque-transmitting member.

2. The ultrasonic diagnostic apparatus according to claim 1, including a liquid ultrasonic permeable medium inlet passage which is formed in the operation section and opens in a portion of said drive passage in the vicinity of the proximal end portion of said insertion section and at a point which lies nearer to the distal end portion of said insertion section than the sealing means; and a liquid ultrasonic permeable medium outlet passage which extends longitudinally throughout the insertion section and through a part of the operation section, and directly communicates with the chamber separately from said drive passage.

3. The ultrasonic diagnostic apparatus according to claim 1, wherein said rotation torque-transmitting member includes a helically wound wire with adjacent turns closely attached to each other, said wire being wound in such a direction as causes said wound wire to be more tightened when rotation torque is transmitted.

4. The ultrasonic diagnostic apparatus according to claim 3, including a tube closely fitted about the outer periphery of said helically wound wire, said tube being formed of a material having a relatively small friction coefficient.

5. The ultrasonic diagnostic apparatus according to claim 1, which comprises a signal cable extending along the rotation torque-transmitting member to transmit a signal to the ultrasonic transducer means and to receive a signal therefrom.

6. The ultrasonic diagnostic apparatus according to claim 1, wherein said chamber forms an opening in operative relation to the ultrasonic scanning member, and which further comprises a balloon prepared from an elastic ultrasonic permeable material for surrounding said opening and for defining a closed space about the distal end portion wherein said space communicates with said chamber through said opening.

7. The ultrasonic diagnostic apparatus according to claim 1, wherein said chamber forms an opening in operative relation to the ultrasonic scanning member, and which further comprises a balloon prepared from an elastic ultrasonic permeable material for surrounding said opening and for defining a closed space about the distal end portion, and a partitioning member prepared from an ultrasonic permeable material and provided at the opening of said chamber to isolate said chamber from the closed space defined by the balloon.

8. The ultrasonic diagnostic apparatus according to claim 7, wherein the closed space defined by said balloon contains a liquid ultrasonic permeable medium.

9. The ultrasonic diagnostic apparatus according to claim 8, wherein the liquid medium in said closed space comprises deaerated water.

10. The ultrasonic diagnostic apparatus according to claim 1, wherein said other end portion of the rotation torque-transmitting member is arranged to extend through the sealing means in liquid tight relation and is prepared from a rigid material which resists distortion by a frictional force arising from said sealing means when rotation torque is transmitted through said member by the drive power source.

11. The ultrasonic diagnostic apparatus according to claim 10, wherein the operation section has a first shaft passage for receiving said other end portion of the rotation torque-transmitting member, and said first shaft passage and said other end portion are arranged to form a first clearance space between their confronting peripheral surfaces, said first clearance space being at least about 0.02 mm in the radial direction.

12. The ultrasonic diagnostic apparatus according to claim 11, wherein the sealing means includes an elastic ring packing seated coaxially in said first shaft passage.

13. The ultrasonic diagnostic apparatus according to claim 1, wherein the rotation torque-transmitting member and said drive passage are arranged to form a second clearance space between their confronting peripheral surfaces for containing the liquid ultrasonic permeable medium, said second clearance space being at least about 0.05 mm in the radial direction.

14. The ultrasonic diagnostic apparatus according to claim 1, wherein said ultrasonic scanning member comprises a rotor including a shaft for coupling with said one end of the rotation torque-transmitting member, the distal end portion forming a second shaft passage within which the rotor shaft is arranged for rotation, wherein said second shaft passage and the rotor shaft form a third clearance space between their confronting peripheral surfaces, said third clearance space being at least about 0.02 mm in the radial direction.

15. The ultrasonic diagnostic apparatus according to claim 1, wherein the liquid ultrasonic permeable medium comprises deaerated water.

16. The ultrasonic diagnostic apparatus according to claim 1, wherein the liquid ultrasonic permeable medium comprises silicone oil.

* * * * *